United States Patent [19]

Clapp et al.

[11] Patent Number: 5,260,215
[45] Date of Patent: Nov. 9, 1993

[54] FUNGAL MICROORGANISM ATCC 74167 CAPABLE OF PRODUCING CHOLESTEROL LOWERING COMPOUNDS

[75] Inventors: Wendy H. Clapp, New York, N.Y.; Yu L. Kong, Edison; Jon D. Polishook, Scotch Plains, both of N.J.

[73] Assignee: Merck & Co., Inc., Rahway, N.J.

[21] Appl. No.: 916,936

[22] Filed: Jul. 20, 1992

[51] Int. Cl.$^5$ .............. C12N 1/14; C12N 1/00
[52] U.S. Cl. .................. 435/254.1; 435/911
[58] Field of Search ............ 424/93 Q; 435/119, 257, 435/911

[56] References Cited

U.S. PATENT DOCUMENTS

| | | | |
|---|---|---|---|
| 4,264,720 | 4/1981 | Marshall et al. | 435/254 |
| 4,294,926 | 10/1981 | Solomons et al. | 435/254 |
| 4,415,661 | 11/1983 | Thiromalachar | 435/254 |
| 4,672,036 | 6/1987 | Bowie et al. | 435/254 |
| 4,687,744 | 8/1987 | Kerwin et al. | 435/254 |
| 4,992,570 | 2/1991 | Nakano et al. | 435/254 |
| 5,021,341 | 6/1991 | Giacobbe et al. | 435/254 |
| 5,026,554 | 6/1991 | Bartizal et al. | 424/404 |
| 5,043,354 | 8/1991 | Tsujii et al. | 435/254 |
| 5,053,425 | 10/1991 | Bartizal et al. | 514/452 |
| 5,055,487 | 10/1991 | Bartizal et al. | 514/452 |
| 5,096,923 | 3/1992 | Bergstrom et al. | 514/452 |
| 5,102,907 | 4/1992 | Bergstrom et al. | 514/456 |
| 5,116,816 | 5/1992 | Dreyfuss et al. | 435/254 |
| 5,137,813 | 8/1992 | Fountoulakis et al. | 435/254 |
| 5,151,365 | 10/1992 | Dombrowski et al. | 435/254 |
| 5,162,211 | 11/1992 | Sesin et al. | 435/254 |

FOREIGN PATENT DOCUMENTS

0450812A1 10/1991 European Pat. Off. .

*Primary Examiner*—Douglas W. Robinson
*Assistant Examiner*—Jeffrey J. Sevingny
*Attorney, Agent, or Firm*—Melvin Winokur; Charles M. Caruso

[57] ABSTRACT

This invention relates to a fungal microorganism MF5757 (ATCC 74167) isolated from bark discs of *Quercus prinus* L. (Chestnut Oak) and useful in a fermentation process to form a compound of formula (I):

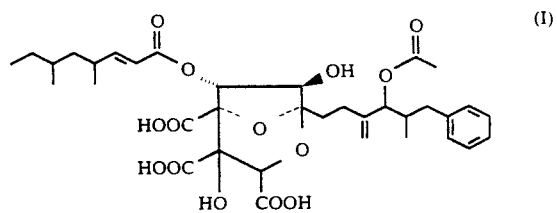

which is a squalene synthetase inhibitor and thus useful as a cholesterol lowering agent.

1 Claim, No Drawings

FUNGAL MICROORGANISM ATCC 74167 CAPABLE OF PRODUCING CHOLESTEROL LOWERING COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e., several grams at a time, and they are not very palatable.

MEVACOR ® (lovastatin) and ZOCOR ® (simvastatin), now commercially available, are members of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analogs containing compounds such as those described in P. Ortiz de Montellano et al, *J. Med. Chem.* 20, 243 (1977) and E. J. Corey and R. Volante, *J. Am. Chem. Soc.*, 98, 1291 (1976). S. Biller (U.S. Pat. No. 4,871,721) describes isoprenoid (phosphinylmethyl) phosphonates as inhibitors of squalene synthetase.

Recently certain nonphosphorous containing inhibitors of squalene synthetase have been isolated as natural products. The compound of formula (I) and its use as a cholesterol lowering agent and antifungal agent is described in U.S. Pat. Nos. 5,096,923 issued Mar. 17, 1992, and 5,053,425 issued Oct. 1, 1991. These patents disclose preparation of compound (I) by an aerobic fermentation procedure employing a fungal culture MF5453 (ATCC 20986). MF5453 is an unidentified sterile fungus isolated from a water sample obtained from the Jalon river in Zaragoza, Spain.

The fungal culture of the present invention (i.e., MF5757) is a previously unseen sterile endophytic strain isolated from bark of *Quercus prinus* L. (Chestnut Oak).

DETAILED DESCRIPTION OF THE INVENTION

The present invention is directed to a novel microorganism that produces compounds of structural formula (I) which are useful as squalene synthetase inhibitors:

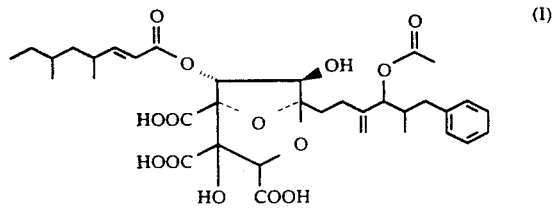

Compound (I) is prepared in an aerobic fermentation procedure employing a novel culture, MF5757, observed as a sterile mycelium. Mutants of MF5757 are also capable of producing compound (I); these mutants have essentially the same characteristics as MF5757. The term "mutant" refers to an MF5757 organism in which some gene of the genome is modified, leaving the gene or genes responsible for the organism's ability to produce recoverable amounts of compound (I) functional and heritable.

The culture employed herein (i.e., MF5757) is isolated from and substantially free from its soil contaminants and free of deleterious viable contaminating microorganisms. That is, the culture is free of contaminating microorganisms that are deleterious to the formation of compound (I).

The culture MF5757 is that of a fungus isolated from the bark of *Quercus prinus* L. (Chestnut Oak) collected near Red Bank, N.J. (Monmouth County). This culture has been deposited with the American Type Culture Collection at 12301 Parklawn Drive, Rockville, Md. 20852 under the terms of the Budapest Treaty as ATCC 74167.

The microorganism MF5757 exhibits the following morphological characteristics:

Colonies 54–56 mm in diameter in 6 days on MYE agar (1% malt extract, 0.2% yeast extract) at 25° C., 50% relative humidity, 12 hour fluorescent light/12 hr dark daily cycle. Culture mat cottony at colony center to felty towards the edge, margin entire, uncolored, 1–2 mm wide. Colony color slate green, Tea Green, Vetiver Green, Andover Green, at the center fading to white at the margin. (Capitalized color names from Ridgeway, R., *Color Standards and Nomenclature*, Washington, D.C. 1912). Reverse uncolored.

Colonies 48–50 mm in diameter in six days on oatmeal agar (Difco) at 25° C., 50% relative humidity, 12 hour fluorescent light/12 hour dark cycle daily. Culture mat woolly to cottony at colony center to felty at colony edge. Colony color olive green, Slate Olive, Sage Green, Pea Green, fading to white at the margin.

On cornmeal agar (Difco), colonies 69–76 mm in diameter in six days at 25° C., 50% relative humidity, 12 hour fluorescent light/12 hour dark cycle daily. Culture mat felty to appressed, mostly uncolored with white cottony tufts approximately halfway between colony center and margin.

Hyphae septate, pale olivaceous green to hyaline, generally 2.0–5.0 μm wide, some segments inflated to 12.0 μm, irregularly branched, differentiated with short staghorn branches and twisted or convoluted areas. No reproductive structures formed on any culture conditions examined.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating mycelia of the producing organism into a suitable medium and then cultivating under aerobic condition.

The fermentation procedure generally is to first inoculate a preserved source of culture into nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably between 200 and 220 rpm. Seed flasks are incubated over a period of 2 to 10 days, preferably 2 to 4 days. When growth is plentiful, usually 2 to 4 days, the culture may be used to inoculate production-medium flasks. A second stage seed growth may be employed, particularly when going into larger vessels. When this is done, a portion of the culture growth is used to inoculate a second seed flask incubated under similar condition but employing shorter time.

After inoculation, the fermentation production medium is incubated for 3 to 30 days, preferably 4 to 22 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.55 to 8.5, most preferably 5.0 to 7.5. After the appropriate period for production of the desired compound, fermentation flasks are harvested and the active compound isolated.

The active compound may then be isolated by several methods including the following:

An alcoholic solvent, possibly mixed with an oxygenated solvent, such as an ester or a ketone, can be employed to extract a compound of this invention from a solid fermentation medium.

The mixture is vigorously stirred and filtered, and the filtrate is concentrated under reduced pressure. Water is added to the concentrate and the pH is adjusted with a mineral acid to between 1 and 4, most preferably between pH 1.5 and 2.5. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane or ethyl acetate.

For extraction of compound (I) from a liquid fermentation, an oxygenated solvent, such as an alcohol, ester, or ketone, can be used. A preferred alcoholic solvent is methanol, in which case the liquid fermentation is treated with two to four volumes of methanol and is then stirred vigorously. The mixture is then filtered and the filtrate is concentrated under reduced pressure. Water is added to the concentrate, the pH is adjusted with mineral acid to between 1 and 4, most preferably between 1.5 and 2.5. The aqueous concentrate is then extracted repeatedly with a water immiscible oxygenated solvent or chlorohydrocarbon solvent. The water immiscible organic layer is decanted and concentrated to dryness. The residue is then further purified as described above for the evaporated organic extract from solid fermentations.

A preferred oxygenated solvent for extraction of liquid fermentations is ethyl acetate. The liquid fermentation is first adjusted with mineral acid to between pH 1 and 4, most preferably between pH 1.5 and 2.5. The mixture is then extracted repeatedly with an oxygenated solvent such as ethyl acetate or 2-butanone. The water immiscible organic layer is decanted and concentrated to dryness. The residue is then further purified as described above for the evaporated organic extract from solid fermentations. Liquid fermentations can also be extracted with 2-butanone without acidification of broth.

The chromatographic separations may be carried out by employing conventional column chromatography with ionic or nonionic resin. Silica gel, such as that available from E. Merck, is a useful adsorbent. When silica gel is the adsorbent, an alcohol/chlorohydrocarbon/organic acid mixture such as methanol/chloroform/acetic acid/water is useful as an eluent. For reverse phase chromatography, the preferred adsorbent is a C8 bonded phase silica gel, although bonded phase silica gels with longer or shorter alkyl residues are also useful. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification. Of particular utility are anion exchange resins such as BioRAD AG4×4 (formate) and Amberlyst A21 (acetate). The active compound can be precipitated out of a nonpolar solvent as the quinine salt. The preferred solvent for precipitation is diethyl ether. The active compound (I) can also be precipitated out of polar solvents, such as methanol, as the ammonium salt.

Alternatively, small scale BioRad AG4×4 anion exchange adsorption/elution of fermentation broth extracts followed by semi-preparative reverse phase chromatography is a useful method for screening for the presence of known and unknown members of the Compound (I) class. Mass spectral analysis of the desalted fractions from this separation can be used to confirm the identify of known compounds.

The following examples illustrate the preparation of compound (I) and are not to be considered as limiting the invention set forth in the claims appended hereto.

The composition of media employed in the following Examples are listed below:

| KFA SEED MEDIUM | |
|---|---|
| | per liter |
| Corn Steep Liquor | 5 g |
| Tomato Paste | 40 g |
| Oat Flour | 10 g |
| Glucose | 10 g |
| *Trace Element Mix | 10 ml |
| Agar | 4 g |
| pH = 6.8 | |

| *Trace Elements Mix | |
|---|---|
| | g/L |
| $FeSO_4.7H_2O$ | 1.0 |
| $MnSO_4.4H_2O$ | 1.0 |
| $CuCl_2.2H_2O$ | 0.025 |
| $CaCl_2$ | 0.1 |
| $H_3BO_3$ | 0.056 |
| $(NH_4)_6Mo_7O_{24}.4H_2O$ | 0.019 |
| $ZnSO_4.7H_2O$ | 0.2 |

Seed medium is dispensed in 54 ml portions into 250 ml unbaffled flasks and is autoclaved for 20 minutes at 121° C. and 15 psi.

| F1 Production Medium | |
|---|---|
| | per 250 ml flask |
| Cracked corn | 10 g |
| **Base liquid | 10 ml |

| **Base Liquid | |
|---|---|
| | g/l |
| Ardamine pH | 0.2 |
| $KH_2PO_4$ | 0.1 |
| $MgSO_4.7H_2O$ | 0.1 |
| Sodium Tartrate | 0.1 |
| $FeSO_4.7H_2O$ | 0.01 |
| $ZnSO_4.7H_2O$ | 0.01 |
| no pH adjustment | |

1. Sterilize for 15 min at 121° C. and 15 psi, and store until needed.
2. On the day of inoculation, add 15 ml distilled $H_2O$, re-autoclave for 20 min at 121° C. and 15 psi, cool to room temperature, and inoculate.

EXAMPLE 1

Preparation of Compound (I)

A. Culturing MF5757

A flask with 54 ml of KFA seed medium in a 250 ml unbaffled Erlenmeyer flask was inoculated with a slant section of the MF5757 culture growth. The KFA seed flask was incubated under aerobic conditions for 3 days at 25° C., 220 rpm, 85% relative humidity. At the end of this incubation, 2.0 ml aliquots were aseptically transferred to F1 production medium flasks. (The fermentation production medium used, F1 medium, was a solid medium in 250 ml flasks). These production flasks were then incubated without agitation at 25° C., 85% relative humidity, with a fermentation cycle of 21 days. Flasks were harvested as follows: 50 ml of methyl ethyl ketone (MEK) was added to the flasks. The grown solid medium was broken and the flasks shaken for 30 minutes.

B. Isolation of Compound (I)

A methyl ethyl ketone extract corresponding to 10 ml of whole broth (i.e., a 10 ml aliquot of the MEK preparation from Step A above) was concentrated to dryness under a stream of nitrogen. The dry extract was redissolved by shaking and sonication in 5 ml of a solution of 6 parts acetonitrile ($CH_3CN$): 4 parts 0.1M sodium formate buffered at pH 4.5 (equilibration buffer), and the solution was extracted with 5 ml of hexanes. A 4.7 ml portion of the aqueous layer was applied to a column of BioRad AG 4-X4 (volume=0.5 ml, formate cycle) anion exchange resin. The resin was prepared as follows: Biorad AG 4-X4 (100-200 mesh, free-base form) was slurried 1:1 with a solution of $CH_3CN/H_2O$ (6/4) and the pH adjusted to 4.5 with concentrated formic acid. One milliliter of the resin slurry was transferred to a glass column and washed with 10 ml of equilibration buffer. After loading the sample, the column was rinsed with 2.5 ml of equilibration buffer followed by 2.5 ml of $CH_3CN/H_2O$ (6/4). The column was eluted with 7.5 ml of a solution of 0.1N $H_2SO_4$ in $CH_3CN/H_2O$ (6/4). A 7.2 ml portion of the eluant was combined with 3 ml of water and extracted with 7.5 ml of ethyl acetate (EtOAc). The EtOAc layer was then concentrated to dryness under nitrogen.

The dry EtOAc layer was dissolved in 1.0 ml of 0.1% $H_3PO_4$ in $CH_3CN/H_2O$ (75/25) and an 860 μl portion was subjected to reverse phase HPLC (Phenomenex Ultracarb 5 ODS 30, 10.0 mm×15 cm, elution 65% $CH_3CN/35\%$ $H_2O+0.1\%$ $H_3PO_4$, flow rate 4.0 ml/min, column temperature 40° C., Waters 990+diode array detection, fraction size 4 ml). Fractions 8 and 9 contained compound (I) and were pooled. The pH of the solution was adjusted to 2.0 with 1.0N HCl and the solution extracted with EtOAc. The EtOAc layer was separated and the solvent removed in vacuo to yield Compound (I) as a yellowish residue. The identity of Compound (I) was confirmed by comparing the fast atom bombardment mass spectral data with that of an authentic sample.

What is claimed is:

1. A biologically pure culture of the fungal microorganism, ATCC 74167, or a mutant thereof wherein the mutant has essentially the same characteristics as ATCC 74167, said culture and mutant thereof being capable of producing a compound of structure:

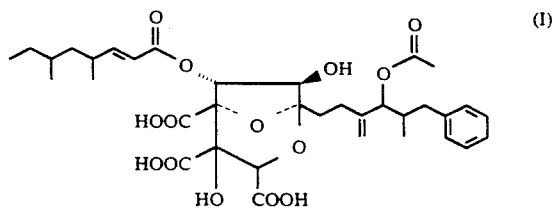

in recoverable amounts.

* * * * *